United States Patent
Lotan et al.

(10) Patent No.: US 8,486,441 B2
(45) Date of Patent: *Jul. 16, 2013

(54) METHODS COMPOSITIONS AND DEVICES UTILIZING STINGING CELLS/CAPSULES FOR DELIVERING A THERAPEUTIC OR A COSMETIC AGENT INTO A TISSUE

(75) Inventors: Tamar Lotan, Jordan Valley (IL); Shimon Eckhouse, Haifa (IL)

(73) Assignee: NanoCyte Inc., Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/955,990

(22) Filed: Nov. 30, 2010

(65) Prior Publication Data

US 2011/0070224 A1    Mar. 24, 2011

Related U.S. Application Data

(60) Continuation of application No. 11/374,969, filed on Mar. 15, 2006, now Pat. No. 8,062,660, which is a continuation of application No. 10/868,802, filed on Jun. 17, 2004, now Pat. No. 7,338,665, which is a division of application No. 10/406,202, filed on Apr. 4, 2003, now Pat. No. 6,923,976, which is a division of application No. 09/963,672, filed on Sep. 27, 2001, now Pat. No. 6,613,344.

(60) Provisional application No. 60/235,910, filed on Sep. 28, 2000.

(51) Int. Cl.
*A61F 13/02*     (2006.01)
*A61L 15/16*    (2006.01)

(52) U.S. Cl.
USPC .......................................................... 424/443

(58) Field of Classification Search
None
See application file for complete search history.

(56) References Cited

U.S. PATENT DOCUMENTS

| | | |
|---|---|---|
| 3,321,188 A | 5/1967 | Unger |
| 3,839,153 A | 10/1974 | Schuurs et al. |
| 3,850,578 A | 11/1974 | Mc Connell |
| 3,850,752 A | 11/1974 | Schuurs et al. |
| 3,853,987 A | 12/1974 | Dreyer |
| 3,879,262 A | 4/1975 | Schuurs et al. |
| 3,984,533 A | 10/1976 | Uzgiris |
| 4,034,074 A | 7/1977 | Miles |
| 4,666,828 A | 5/1987 | Gusella |
| 4,801,531 A | 1/1989 | Frossard |
| 5,073,488 A | 12/1991 | Matner et al. |
| 5,162,378 A | 11/1992 | Guthauser |
| 5,192,659 A | 3/1993 | Simons |

(Continued)

FOREIGN PATENT DOCUMENTS

| | | |
|---|---|---|
| EP | 1519755 | 4/2005 |
| WO | WO 98/29134 | 7/1998 |

(Continued)

OTHER PUBLICATIONS

Official Action Dated Oct. 19, 2011 From the US Patent and Trademark Office Re. U.S. Appl. No. 13/166,877.

(Continued)

*Primary Examiner* — Carlos Azpuru

(57) ABSTRACT

A composition of matter including at least one stinging capsule comprising a therapeutic or cosmetic agent is described.

19 Claims, 10 Drawing Sheets
(7 of 10 Drawing Sheet(s) Filed in Color)

U.S. PATENT DOCUMENTS

| | | | |
|---|---|---|---|
| 5,272,057 | A | 12/1993 | Smulson et al. |
| 5,362,442 | A | 11/1994 | Kent |
| 5,641,508 | A | 6/1997 | Li et al. |
| 5,885,211 | A | 3/1999 | Eppstein et al. |
| 5,885,260 | A | 3/1999 | Mehl, Sr. et al. |
| 6,019,967 | A | 2/2000 | Breton et al. |
| 6,022,316 | A | 2/2000 | Eppstein et al. |
| 6,132,747 | A | 10/2000 | Lotan |
| 6,338,837 | B1 | 1/2002 | Lotan |
| 6,406,709 | B1 | 6/2002 | Lotan |
| 6,416,960 | B1 | 7/2002 | Bryan |
| 6,596,531 | B2 | 7/2003 | Campbell et al. |
| 6,613,344 | B2 * | 9/2003 | Lotan et al. ............ 424/434 |
| 6,613,744 | B2 * | 9/2003 | Wozney et al. ............ 514/8.8 |
| 6,923,976 | B2 * | 8/2005 | Lotan et al. ............ 424/401 |
| 7,338,665 | B2 * | 3/2008 | Lotan et al. ............ 424/443 |
| 7,611,723 | B2 | 11/2009 | Lotan et al. |
| 7,632,522 | B2 * | 12/2009 | Lotan et al. ............ 424/520 |
| 7,998,509 | B2 * | 8/2011 | Lotan et al. ............ 424/520 |
| 8,062,660 | B2 * | 11/2011 | Lotan et al. ............ 424/443 |
| 8,287,912 | B2 * | 10/2012 | Lotan et al. ............ 424/520 |
| 2001/0004715 | A1 | 6/2001 | Duran et al. |
| 2002/0039592 | A1 | 4/2002 | Lotan et al. |
| 2003/0189850 | A1 | 10/2003 | Sasaki et al. |
| 2003/0202995 | A1 | 10/2003 | Lotan et al. |
| 2004/0224013 | A1 | 11/2004 | Lotan et al. |
| 2004/0235143 | A1 | 11/2004 | Sasaki et al. |
| 2005/0181978 | A1 | 8/2005 | Rojkjaer et al. |
| 2006/0039897 | A1 | 2/2006 | Lotan et al. |
| 2007/0160546 | A1 | 7/2007 | Lotan et al. |
| 2010/0055058 | A1 | 3/2010 | Lotan et al. |
| 2011/0250245 | A1 | 10/2011 | Lotan et al. |

FOREIGN PATENT DOCUMENTS

| | | |
|---|---|---|
| WO | WO 99/44507 | 9/1999 |
| WO | WO 99/44508 | 9/1999 |
| WO | WO 99/44637 | 9/1999 |
| WO | WO 99/44638 | 9/1999 |
| WO | WO 00/03758 | 1/2000 |
| WO | WO 00/04821 | 2/2000 |
| WO | WO 00/04832 | 2/2000 |
| WO | WO 00/15102 | 3/2000 |
| WO | WO 01/37778 | 5/2001 |
| WO | WO 02/26191 | 4/2002 |
| WO | WO 03/079967 | 10/2003 |

OTHER PUBLICATIONS

Response Dated Jun. 14, 2011 to Official Action of Apr. 11, 2011 From the US Patent and Trademark Office Re.: U.S. Appl. No. 11/374,969.
Restriction Official Action Dated Dec. 2, 2011 From the US Patent and Trademark Office Re. U.S. Appl. No. 12/588,368.
Response Dated Nov. 21, 2011 to Official Action of Oct. 19, 2011 From the US Patent and Trademark Office Re. U.S. Appl. No. 13/166,877.
"Skin, Hair, and Nails", http://web.archive.org/web.20030404084846/www.kidshealth.org/PageManager.jsp?dn=Kidshealth&lic=1&ps=107&cat_id-20090&article_set-20552, p. 1-7, 2003.
Communication Pursuant to Article 94(3) EPC Dated Feb. 2, 2010 From the European Patent Office Re.: Application No. 01976586.6.
Communication Pursuant to Article 94(3) EPC Dated Dec. 17, 2008 From the European Patent Office Re.: Application No. 01976586.6.
International Preliminary Report on Patentability Dated Dec. 11, 2008 From the International Bureau of WIPO Re.: Application No. PCT/IL2006/000465.
International Preliminary Report on Patentability Dated May 18, 2007 From the International Bureau of WIPO Re.: Application No. PCT/IL2005/001127.
International Search Report Dated Jun. 22, 2006 From the International Searching Authority Re.: Application No. PCT/IL05/01127.
International Search Report Dated Jun. 24, 2008 From the International Searching Authority Re.: Application No. PCT/IL2006/000465.
Notice of Allowance Dated Aug. 6, 2009 From the US Patent and Trademark Office Re.: U.S. Appl. No. 11/328,221.
Notice of Allowance Dated Jun. 19, 2009 From the US Patent and Trademark Office Re.: U.S. Appl. No. 10/507,692.
Office Action Dated Sep. 2, 2010 From the Israeli Patent Office Re.: Application No. 155097 and Its Translation Into English.
Office Action Dated Jun. 4, 2008 From the Israeli Patent Office Re.: Application No. 164191.
Office Action Dated Jul. 7, 2008 From the Israeli Patent Office Re.: Application No. 155097.
Office Action Dated Feb. 15, 2009 From the Israeli Patent and Trademark Office Re.: Application No. 155097 and Its Translation Into English.
Office Action Dated Jun. 20, 2007 From the Israeli Patent Office Re.: Application No. 155097.
Office Action Dated Nov. 23, 2009 From the Israeli Patent Office Re.: Application No. 155097 and Its Translation Into English.
Office Action Dated Jul. 29, 2010 From the Israel Patent Office Re. Application No. 199236 and Its Translation Into English.
Office Action Dated Jul. 29, 2010 From the Israeli Patent Office Re.: Application No. 164191 and Its Translation Into English.
Official Action Dated Nov. 1, 2007 From the US Patent and Trademark Office Re.: U.S. Appl. No. 11/328,221.
Official Action Dated Oct. 4, 2006 From the US Patent and Trademark Office Re.: U.S. Appl. No. 10/868,802.
Official Action Dated Oct. 4, 2007 From the US Patent and Trademark Office Re.: U.S. Appl. No. 10/507,692.
Official Action Dated Jun. 6, ,2006 From the US Patent and Trademark Office Re.: U.S. Appl. No. 10/981,522.
Official Action Dated Oct. 9, 2008 From the US Patent and Trademark Office Re.: U.S. Appl. No. 11/328,221.
Official Action Dated Jul. 10, 2008 From the US Patent and Trademark Office Re.: U.S. Appl. No. 11/108,662.
Official Action Dated Jul. 10, 2009 From the US Patent and Trademark Office Re.: U.S. Appl. No. 11/108,662.
Official Action Dated Apr. 13, 2009 From the US Patent and Trademark Office Re.: U.S. Appl. No. 11/328,221.
Official Action Dated Aug. 13, 2007 From the US Patent and Trademark Office Re.: U.S. Appl. No. 11/108,662.
Official Action Dated Dec. 15, 2006 From the US Patent and Trademark Office Re.: U.S. Appl. No. 11/328,221.
Official Action Dated Jul. 17, 2008 From the US Patent and Trademark Office Re.: U.S. Appl. No. 11/328,221.
Official Action Dated Nov. 17, 2008 From the US Patent and Trademark Office Re.: U.S. Appl. No. 10/507,692.
Official Action Dated Jun. 18, 2010 From the US Patent and Trademark Office Re.: U.S. Appl. No. 12/616,801.
Official Action Dated Sep. 20, 2007 From the US Patent and Trademark Office Re.: U.S. Appl. No. 10/981,522.
Official Action Dated Jan. 24, 2008 From the US Patent and Trademark Office Re.: U.S. Appl. No. 10/507,692.
Official Action Dated Sep. 24, 2010 From the US Patent and Trademark Office Re.: U.S. Appl. No. 12/616,801.
Official Action Dated Apr. 25, 2008 From the US Patent and Trademark Office Re.: U.S. Appl. No. 10/981,498.
Official Action Dated Jul. 26, 2007 From the US Patent and Trademark Office Re.: U.S. Appl. No. 10/981,498.
Official Action Dated Mar. 27, 2009 From the US Patent and Trademark Office Re.: U.S. Appl. No. 10/507,692.
Official Action Dated Apr. 28, 2006 From the US Patent and Trademark Office Re.: U.S. Appl. No. 10/868,802.
Official Action Dated Dec. 28, 2007 From the US Patent and Trademark Office Re.: U.S. Appl. No. 10/981,522.
Official Action Dated Nov. 29, 2006 From the US Patent and Trademark Office Re.: U.S. Appl. No. 10/981,522.
Official Action Dated Mar. 30, 2007 From the US Patent and Trademark Office Re.: U.S. Appl. No. 11/328,221.
Official Action Dated May 30, 2006 From the US Patent and Trademark Office Re.: U.S. Appl. No. 10/981,498.
Official Action Dated Nov. 30, 2006 From the US Patent and Trademark Office Re.: U.S. Appl. No. 10/981,498.
Official Action Dated Jan. 31, 2008 From the US Patent and Trademark Office Re.: U.S. Appl. No. 11/108,662.

Response Dated Dec. 9, 2009 to Official Action of Jul. 10, 2009 From the US Patent and Trademark Office Re.: U.S. Appl. No. 11/108,662.
Response Dated Aug. 10, 2010 to Phone Conversation of Aug. 1, 2010 With the Examiner Re. Application No. 155097.
Response Dated Aug. 10, 2010 to Phone Conversation of Aug. 1, 2010 With the Examiner Re. Application No. 199236.
Response Dated Jul. 14, 2010 to Official Action of Jun. 18, 2010 From the US Patent and Trademark Office Re.: U.S. Appl. No. 12/616,801.
Response Dated May 17, 2010 to Communication Pursuant to Article 94(3) EPC of Feb. 2, 2010 From the European Patent Office Re.: Application No. 01976586.6.
Response Dated Dec. 22, 2010 to Official Action of Sep. 24, 2010 From the US Patent and Trademark Office Re.: U.S. Appl. No. 12/616,801.
Response Dated Feb. 22, 2010 to Office Action of Nov. 23, 2009 From the Israeli Patent Office Re.: Application No. 155097.
Response Dated Nov. 22, 2010 to Office Action of Jul. 29, 2010 From the Israel Patent Office Re. Application No. 199236.
Response Dated Nov. 22, 2010 to Office Action of Jul. 29, 2010 From the Israeli Patent Office Re.: Application No. 164191.
Response Dated Nov. 24, 2010 to Office Action of Sep. 2, 2010 From the Israeli Patent Office Re.: Application No. 155097.
Response Dated Dec. 30, 2009 to Office Action of Jun. 25, 2009 From the Israel Patent Office Re.: Application No. 164191.
Supplementary Partial European Search Report Dated Feb. 6, 2007 From the European Patent Office Re.: Application No. 01976586.6.
Written Opinion Dated Jun. 22, 2006 From the International Searching Authority Re.: Application No. PCT/IL05/01127.
Written Opinion Dated Jun. 24, 2008 From the International Searching Authority Re.: Application No. PCT/IL2006/000465.
Anderluh et al. "A Common Motif in Proparts of Cnidarian Toxins and Nematocyst Collagens and Its Putative Role", Biochimica et Biophysica Acta, 1476: 372-376, 2000.
Anderson et al. "A Triploblast Origin for Myxozoa?", Nature, 392(6674): 346-347, 1998.
B?ttger et al. "GFP Expression in Hydra: Lessons From the Particle Gun", Development of Gene Evolution, 212: 302-305, 2002.
Bode "The Interstitial Cell Lineage of Hydra: A Stem Cell System That Arose Early in Evolution", Journal of Cell Science, 109: 1155-1164, 1996.
Brennecke et al. "The Lack of A Stress Response in Hydra Oligactis Is Due to Reduced Hsp70 mRNA Stability", European Journal of Biochemistry, 255: 703-709, 1998.
Chapman et al. "Cytological Studies of the Nematocysts of Hydra. I. Desmonemes, Isorhizas, Cnidocils, and Supporting Structures", Journal of Biophysical nad Biochemical Cytology, 5(1): 69-78, Plates 22-27, 1959.
Cikala et al. "Expression of GFP-Fusion Protein in Hydra to Investigate the Function of Genes Linked With Apoptosis", International Workshop—Evangelische Akademie, Tutzing/Germany, 2001.
Engel et al. "A Switch in Disulfide Linkage During Minicollagen Assembly in Hydra Newmatocysts", The EMBO Journal, 20(12):3063-3073, 2001.
Engel et al. "Atomic Force Microscopy: A Powerful Tool to Observe Biomolecules at Work", Trends in Cell Biology, 9:77-80, 1999.
Fernadez-Alonso et al. "DNA Vaccination by Immersion and Ultrasound to Trout Viral Heamorrhagic Septicaemia Virus", Vaccine, 19: 3067-3075, 2001.
Gerke et al. "The Spatial Distribution of Cations in Nematocytes of Hydra Vulgaris", Hydrobiologia, 216/217: 661-669, 1991.
Godknecht et al. "Discharge and Mode of Action of the Tentacular Nematocysts of Anemonia Sulcata (Antozoa: Cnidaria)", Marine Biology, 100: 83-92, 1988.
Heeger et al. "Protection of Human Skin Against Jellyfish (*Cyanea Capillata*) Stings", Marine Biology, 113: 669-678, 1992. Abstract.
Hidaka "Mechanism of Nematocyst Discharge and Its Cellular Control", Advances in Comparative and Environment Physiology, 15(Chap.2): 45-76, 1993.
Hidaka et al. "Effects of Calcium on the Mechanical Properties of the Capsule Wall of Isolated Nematocysts From Calliactis Polypus", Comparisons in Biochemistry and Physiology, 107A(1): 31-36, 1994.

Hiroshi et al. "Chemical Characterization of the Nematocyst Toxin From the Hawaiian Jellyfish Carybdea Alata", Symposium on the Chemistry of Natural Products, Symposium Papers, 42: 391-396, 2000. Abstract.
Holstein et al. "An Ultrahigh-Speed Analysis of Exocytosis: Nematocyst Discharge", Science, New Series, 223(4638): 830-833, 1984.
Hyde "Skin, Hair, and Nails", The Nemours Foundation, Kidshealth, Retrieved From the Internet, p. 1-7, Apr. 21, 2001.
Kass-Simon et al. "The Behavioral and Developmental Physiology of Nematocysts", Canadian Journal of Zoology, 80: 1772-1794, 2002.
Kimball et al. "Efficacy of a Jellyfish Sting Inhibitor in Preventing Jellyfish Stings in Normal Volunteers", Wilderness and Environmental Medicine, 15: 102-108, 2004.
Koch et al. "Spinalin, A New Glycine- and Histidine-Rich Protein in Spines of Hydra Nematocysts", Journal of Cell Science, 111: 1545-1554, 1998.
Lohmann et al. "Silencing of Developmental Genes in Hydra", Developmental Biology, 214: 211-214, 1999.
Lotan et al. "Delivery of A Nematocyst Toxin", Nature, XP008041281, 375(6531): 456, Jun. 8, 1995.
Lotan et al. "Toxin Compartmentation and Delivery in the Cnidaria: The Nematocyst's Tubule as a Multiheaded Poisonous Arrow", The Journal of Experimental Zoology, 275(6): 444-451, 1996.
Lubbock "Chemical Recognition and Nematocyte Exitation in A Sea Anemone", Journal of Experimental Biology, 83: 283-292, 1979.
Lubbock et al. "Removal of Bound Calcium From Nematocyst Contents Causes Discharge", Nature, 290(5806): 500-501, 1981.
Marchini et al. "A Fast Centrifuge Method for Nematocyst Isolation From Pelagia Noctiluca Forskal (Cnidaria: Scyphozoa)", Rivista di Biologia, Biology Forum, 97: 505-516, 2004.
Marino et al. "Regulatory Volume Increase in Nematocysts Isolated From Acontia of Aiptasia Diaphana (Cnidaria, Anthozoa)", Cellular and Molecular Biology, 50: 533-542, 2004.
Miljkovic et al. "Cnidarian and Bilaterian Promoters Can Direct GFP Expression in Transfected Hydra", Development Biology, 246: 377-390, 2002.
Miljovic et al. "GFP Expression in Hydra", International Workshop—Evangelische Akademie, Tutzing/Germany, 2001. Abstract.
Murate et al. "Hydra Regeneration From Recombinant Ectodermal and Endodermal Tissue—II. Differential Stability in the Ectodermal and Endodermal Epithelial Organization", Journal of Cell Science, 110: 1155-1164, 1997.
Opalinska et al. "Nucleic-Acid Therapeutics: Basic Principles and Recent Applications", Nature Reviews: Drug Delivery, 1: 503-514, 2002.
Ozbek et al. "A Switch in Disulfide Linkage During Minicollagen Assembly in Hydra Nematocysts", The EMBO Journal, 20(12): 3063-3073, 2001. Abstract.
Robson "Nematocysts of Corynactis: The Activity of the Filament During Discharge", Quarterly Journal of Microscopical Science, 94(Part 3): 229-235, Sep. 1953.
Salleo et al. "Release of Free CA2+ From the Nematocysts of Aiptasia Mutabilis During the Discharge", Physiology & Zoology, 61(3): 272-279, 1988.
Sharp "RNAi and Double-Strand RNA", Genes & Development, 13: 139-141, 1999.
Siddall et al. "The Demise of a Phylum of Protists: Phylogeny of Myxozoa and Other Parasitic Cnidaria", Journal of Parasitology, 81(6): 961-967, 1995.
Smothers et al. "Molecular Evidence That the Myxozoan Protists Are Metazoans", Science, 265(5179): 1719-1721, 1994.
Stauffer et al. "Common Florida Injuries", Empulse, 8(3.2): 11-14, 2003.
Tardent "The Cnidarian Cnidocyte, A High-Tech Cellular Weaponry", BioEssays, XP00804143, 17(4): 351-362, 1995.
Tardent et al. "Morphology and Morphodynamics of the Stenotele Nematocyst of Hydra Attenuata Pall (Hydrozoa, Cnidaria)", Cell Tissue Research, 224(2): 269-290, 1982.
Thorington et al. "Control of Cnida Discharge: I. Evidence for Two Classes of Chemoreceptor", Biological Bulletin, 174: 163-171, 1988.
Verma et al. "The Achilles Heel of Gene Therapy", Genes and Resistance to Diseases, p. 148, 2000.

Wang et al. "Isolation and Characterization of a Mini-Collagen Gene Encoding A Nematocyst Capsule Protein From a Reef-Building Coral, Acropora Donei", Gene, 152(2): 195-200, 1995. Abstract.

Watson et al. "Cnidocyte Mechanoreceptors Are Tuned to the Movements of Swimming Prey by Chemoreceptors", Science, 243: 1589-1591, 1989.

Watson et al. "Receptors for N-Acetylated Sugars May Stimulate Adenylate Cyclase to Sensitize and Tune Mechanoreceptors Involved in Triggering Nematocyst Discharge", Experimental Cell Research, 198(1): 8-16, 1992.

Weber "Nematocysts (Stinging Capsules of Cnidaria) as Donnan-Potential-Dominated Osmotic Systems", European Journal of Biochemistry, 184(2): 465-476, 1989.

Weber et al. "Some Physical and Chemical Properties of Purified Nematocysts of Hydra Attenuata Pall. (Hydrozoa, Cnidaria)", Comparative Biochemistry and Physiology, 88B(3): 855-862, 1987.

Westfall et al. "Ultrastructure of the Dinoflagellate Polykrikos. I. Development of the Nematocyst-Taeniocyst Complex and Morphology of the Site for Extrusion", Journal of Cell Science, 63: 245-261, 1983.

Wittlieb et al. "Transgenic Hydra Allow in Vivo Tracking of Individual Stem Cells During Morphogenesis", PNAS, Early Edition: 1-4, 2006.

Office Action Dated Feb. 27, 2011 From the Israeli Patent Office Re. : Application No. 164191 and Its Translation Into English.

Notice of Allowance Dated Aug. 16, 2011 From the US Patent and Trademark Office Re.: U.S. Appl. No. 11/374,969.

Office Action Dated Apr. 11, 2011 From the US Patent and Trademark Office Re.: U.S. Appl. No. 11/374,969.

Notice of Allowance Dated Mar. 24, 2011 From the US Patent and Trademark Office Re. : U.S. Appl. No. 12/616,801.

Response Dated May 15, 2011 to Office Action of Feb. 27, 2011 From the Israeli Patent Office Re.: Application No. 164191.

Official Action Dated Feb. 16, 2012 From the US Patent and Trademark Office Re. U.S. Appl. No. 12/588,368.

Official Action Dated Jun. 5, 2012 From the US Patent and Trademark Office Re. U.S. Appl. No. 12/588,368.

Summons to Attend Oral Proceedings Pursuant to Rule 115(1) EPC Dated Feb. 16, 2012 From the European Patent Office Re.: Application No. 01976586.6.

Official Action Dated Dec. 21, 2011 From the US Patent and Trademark Office Re. U.S. Appl. No. 13/166,877.

Notice of Allowance Dated Jun. 14, 2012 From the US Patent and Trademark Office Re. U.S. Appl. No. 13/166,877.

Communication Under Rule 71(3) EPC Dated Sep. 21, 2012 From the European Patent Office Re. Application No. 01976586.6.

Office Action Dated Dec. 23, 2012 From the Israel Patent Office Re. Application No. 199236 and Its Translation Into English.

Notice of Allowance Dated Aug. 22, 2012 From the US Patent and Trademark Office Re. U.S. Appl. No. 12/588,368.

* cited by examiner

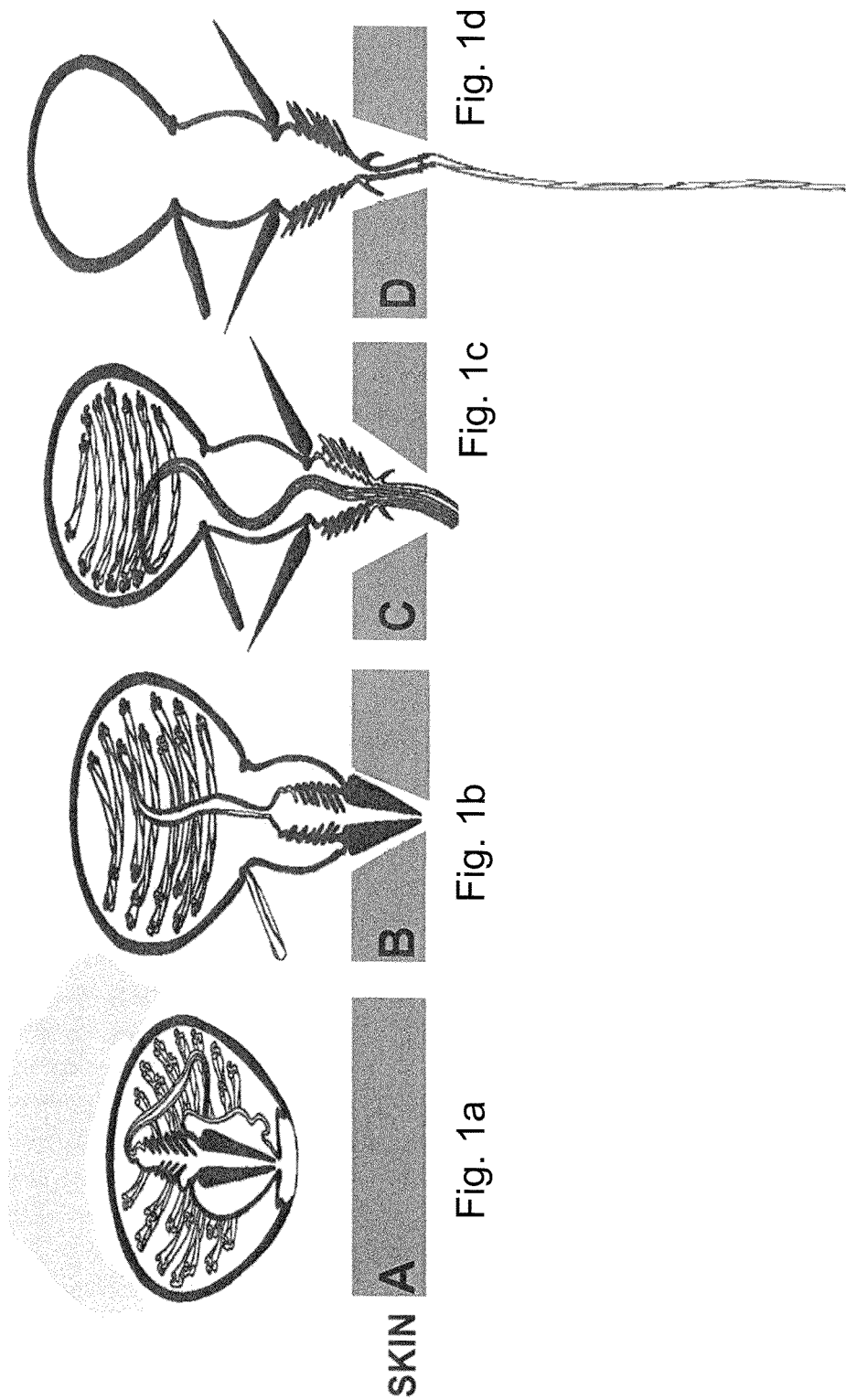

METHODS COMPOSITIONS AND DEVICES UTILIZING STINGING CELLS/CAPSULES FOR DELIVERING A THERAPEUTIC OR A COSMETIC AGENT INTO A TISSUE

RELATED APPLICATIONS

This application is a continuation of U.S. patent application Ser. No. 11/374,969, filed on Mar. 15, 2006, which is a continuation of U.S. patent application Ser. No. 10/868,802, filed on Jun. 17, 2004, now U.S. Pat. No. 7,338,665, which is a divisional of U.S. patent application Ser. No. 10/406,202, filed on Apr. 4, 2003, now U.S. Pat. No. 6,923,976, which is a divisional of U.S. patent application Ser. No. 09/963,672, filed on Sep. 27, 2001, now U.S. Pat. No. 6,613,344, which claims the benefit of U.S. Provisional Patent Application No. 60/235,910, filed on Sep. 28, 2000. The contents of the above applications are all incorporated by reference.

FIELD AND BACKGROUND OF THE INVENTION

The present invention relates to stinging cells or capsules and to the use thereof in compositions, devices and methods for delivering a therapeutic, cosmetic or diagnostic agent into a tissue. More particularly, the present invention relates to the use of stinging cells or capsules as transdermal/intradermal, transmembranal or transcuticular delivery devices.

Therapeutic agents such as drugs are a mainstay of modern medicine and are used for the prevention, diagnosis, alleviation, treatment, or cure of diseases.

Biological, biochemical and/or physical barriers often limit delivery of therapeutic agents to target tissue. For example, skin and/or various organ membranes are physical barriers, which must be traversed by a topically administered drug targeted at internal tissues. Orally administered drugs must be resistant to the low pH conditions and digestive enzymes present in the gastrointestinal (GI) tract.

To traverse such barriers, drugs targeted at internal tissues are often administered via a transdermal injection, using a syringe and a needle or other mechanical devices. A transdermal injection delivers drugs into the subcutaneous space thus traversing the epidermis-dermis layers.

Anatomically, the skin of a human body is subdivided into three compartments: an epidermis, a dermis and a subcutaneous layer, of which the epidermis plays a key role in blocking drug delivery via the skin (the dourest layer of the epidermis is the stratum corneum which is called also the horny layer). The epidermis is 0.1 mm or more in thickness and consists mainly of protein surrounded by lipid, thus rendering the epidermis hydrophobic.

Although the syringe and needle is an effective delivery device, it is sensitive to contamination, while use thereof is often accompanied by pain and/or bruising. In addition, the use of such a device is accompanied by risk of accidental needle injury to a health care provider.

Mechanical injection devices based on compressed gases have been developed to overcome the above-mentioned limitations of syringe and needle devices. Such devices typically utilize compressed gas (such as, helium or carbon dioxide) to deliver medications at high velocity through a narrow aperture.

Although such devices traverses some of the limitations mentioned above, their efficiency is medication dependent, and their use can lead to pain, bruising and lacerations.

Other less common delivery methods utilize a pulsed Yag laser to punctuate the stratum corneum in order to deliver medication via diffusion and enhancement of ionic compound flux across the skin by the application of an electric current. Although such methods are effective in delivering small charged molecules, a danger of skin burns accompanies their use.

Non-invasive methods, which overcome some of the limitations inherent to the invasive delivery methods described above, have also been described. Such methods utilize preparations, which include an active ingredient disposed within lipid vehicles (e.g., liposomes) or micelles or accompanied with skin permeation agent such that absorption of the active ingredient through the skin is enhanced. Such preparations can be directly applied to a skin region or delivered via transdermal devices such as membranes, pressure-sensitive adhesive matrices and skin patches.

In transdermal delivery, the active ingredient penetrates the skin and enters the capillary blood or the lymph circulation system, which carries the drug to the target organ or to the tissue or has a local effect.

For several years, transdermal drug delivery systems have been employed to effectively introduce a limited number of drugs through unbroken skin. Aside from comfort and convenience, transdermal systems avoid the barriers, delivery rate control problems and potential toxicity concerns associated with traditional administration techniques, such as oral, intramuscular or intravenous delivery.

Although transdermal delivery offers an alternative to some invasive delivery methods, the efficiency thereof is affected by the physical and chemical properties of a drug and physiological or pathological parameters such as the skin hydration, temperature, location, injury, and the body metabolism.

To overcome the limitations of invasive and non-invasive delivery devices, the present inventors propose the use of "stinging cells" (e.g. cnidocytes, nematocytes and the like) or "stinging capsules" (e.g., cnidocysts, nematocysts and polar capsules) isolated therefrom for tissue delivery of a therapeutic or cosmetic agents.

Cnidaria (hydras, sea anemones, jellyfish and corals) are aquatic animals, which possess a variety of compounds which are stored and delivered via specialized capsules (cnidocysts), which form a part of specialized cells termed stinging cells (cnidocytes, nematocytes, ptychocytes and the like). The stinging capsules act as microscopic syringes and serve as a prey or defense mechanism. The Cnidaria family which encompasses 10,000 known species, includes sedentary single or colonial polyps and pelagic jellyfish. In some of these species, cnidocytes account for more than 45% of the cells present (Tardent 1995).

As shown in FIGS. 1a-d, a cnidocyst is a hardened dense capsule, filled with liquid containing a highly folded inverted tubule which sometimes features specialized structures such as shafts, barbs, spines, and/or stylets. In nature, the cnidocyst discharges and releases its tubule (FIG. 1d) into tissue following physical or chemical triggering.

Discharge is initiated by a rapid osmotic influx of water which generates an internal hydrostatic (liquid) pressure of 150 atmospheres forcing capsule rupture and ejection of the tubule (Holstein and Tardent 1984). During ejection, the long coiled and twisted tubule is averted and its length increases by 95 percent. Accelerating at 40,000 g, the tubule untwists to generate a torque force, which rotates the tubule several times around its axis. These mechanical processes generate a powerful driving force, which enables efficient delivery of the compounds, the toxins and enzymes stored within the capsule (Lotan et al. 1995, 1996; Tardent 1995). This process, which occurs within microseconds, is among the most rapid exocytosis events in biology (Holstein and Tardent 1984).

There are at least three dozen known types of cnidocysts (also termed cnidae) including more than 30 varieties of nematocysts found in most Cnidaria and spirocysts, and ptychocysts found mainly in the Cnidaria class Anthozoa (Mariscal 1974).

As is further detailed herein, the present invention utilizes stinging cells such as cnidocytes, or stinging capsules (cnidocysts) isolated therefrom for efficiently delivering agents into a tissue while being devoid of the limitations inherent to prior art invasive or non-invasive delivery devices and compositions.

SUMMARY OF THE INVENTION

According to one aspect of the present invention there is provided a composition of matter comprising a therapeutic or a cosmetic agent and at least one stinging capsule.

According to another aspect of the present invention there is provided a pharmaceutical composition comprising as an active ingredient a therapeutic or cosmetic agent, at least one stinging capsule and a pharmaceutically acceptable carrier.

According to yet another aspect of the present invention there is provided a delivery device comprising: (a) at least one stinging capsule capable of delivering upon discharge liquid disposed in or around the at least one stinging capsule into a tissue; and (b) a support being for: (i) supporting the at least one stinging capsule; and (ii) applying the at least one stinging capsule to an outer surface of the tissue.

According to further features in preferred embodiments of the invention described below, the at least one stinging capsule includes a plurality of stinging capsules attached to the support in a manner so as to form a tattoo making device.

According to still another aspect of the present invention there is provided a method of delivering a therapeutic or a cosmetic agent into a tissue, the method comprising the steps of: (a) applying a composition of matter including the therapeutic or cosmetic agent disposed in or around at least one stinging capsule to an outer surface of the tissue; and (b) triggering a discharge of the at least one stinging capsule to thereby deliver the therapeutic or the cosmetic agent into the tissue.

According to an additional aspect of the present invention there is provided a method of delivering a therapeutic or a cosmetic agent into a tissue, the method comprising the steps of: (a) applying a composition including, as an active ingredient, at least one therapeutic or cosmetic agent onto an outer surface of the tissue; and (b) applying at least one stinging capsule to the outer surface of the tissue; and (c) triggering a discharge of the at least one stinging capsule to thereby deliver the therapeutic or the cosmetic agent into a tissue.

According to yet an additional aspect of the present invention there is provided a method of preparing a delivery capsule, the method comprising the steps of: (a) isolating an intact stinging capsule from an organism; and (b) treating the stinging capsule under conditions which inactivate an endogenous toxin stored in the stinging capsule yet do not trigger discharge or breakdown of the stinging capsule to thereby obtain the delivery capsule.

According to still an additional aspect of the present invention there is provided a delivery device comprising a stinging capsule, wherein an endogenous toxin stored by the isolated stinging capsule is non-functional.

According to further features in preferred embodiments of the invention described below, the therapeutic or cosmetic agent is disposed in a liquid surrounding, or stored within, the at least one stinging capsule.

According to still further features in the described preferred embodiments the therapeutic agent is selected from the group consisting of a drug, a nucleic acid construct, a vaccine, a hormone, an enzyme and an antibody.

According to still further features in the described preferred embodiments the therapeutic agent is a prodrug activatable prior to, during or following discharge of the at least one stinging capsule.

According to still further features in the described preferred embodiments the cosmetic agent is selected from the group consisting of a cosmetic dye, an anti wrinkling agent, an anti-acne agent, a vitamin, a skin peel agent, a hair follicle stimulating agent and a hair follicle suppressing agent.

According to still further features in the described preferred embodiments the stinging capsule can be an isolated stinging capsule or it can form a part of an isolated stinging cell.

According to still further features in the described preferred embodiments the at least one stinging capsule is capable of delivering the therapeutic or cosmetic agent into a tissue.

According to still further features in the described preferred embodiments the endogenous toxin naturally stored within the at least one stinging capsule is substantially non-toxic to mammals.

According to still further features in the described preferred embodiments the endogenous toxin is non-functional.

According to still further features in the described preferred embodiments the at least one stinging capsule is derived from an organism of a class selected from the group consisting of Anthozoa, Hydrozoa and Scyphozoa.

According to still further features in the described preferred embodiments the at least one stinging capsule is derived from a stinging cell of an organism of a phylum selected from the group consisting of Cnidaria, Dinoflagellata and Myxozoa. According to still further features in the described preferred embodiments the at least one stinging cell forms a part of at least a tentacle portion of an organism of the phylum Cnidaria.

According to still further features in the described preferred embodiments the pharmaceutically acceptable carrier is selected from the group consisting of an aqueous solution, a gel, and an oil and semi solid formulation.

According to still further features in the described preferred embodiments the device further comprising a mechanism for triggering the discharge of the at least one stinging capsule.

According to still further features in the described preferred embodiments the mechanism is selected from the group consisting of a chemical triggering mechanism and an electrical triggering mechanism.

According to still further features in the described preferred embodiments the support is selected from the group consisting of a patch, a foil, a plaster and a film.

According to still further features in the described preferred embodiments the step of triggering is effected by a change in pH, a chemical substance, a mechanical force or contact between the at least one stinging capsule and the outer surface of the tis sue.

According to still further features in the described preferred embodiments the organism is of a phylum selected from the group consisting of Cnidaria, Dinoflagellata and Myxozoa.

According to still further features in the described preferred embodiments the step of treating the stinging capsule under conditions which inactivate an endogenous toxin stored in the stinging capsule yet do not trigger discharge or breakdown of the stinging capsule to thereby obtain the delivery capsule) is effected by incubating the stinging capsule at a temperature of 37-45° C. for at least two hours.

The present invention successfully addresses the shortcomings of the presently known configurations by providing a natural source for delivering therapeutic and cosmetic agents. By exploiting one of the most efficient system that exist in biology it is possible to use stinging capsules as delivery capsules for drugs, vaccines, antibodies, DNA constructs and other agents.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. The patent or application file contains at least one drawing executed in color. Copies of this patent or patent application publication with color drawing(s) will be provided by the Office upon request and payment of the necessary fee.

In the drawings:

FIGS. 1a-d illustrate the structure and release mechanism of a cnidocyst;

DESCRIPTION OF THE PREFERRED EMBODIMENTS

Figure 2A:
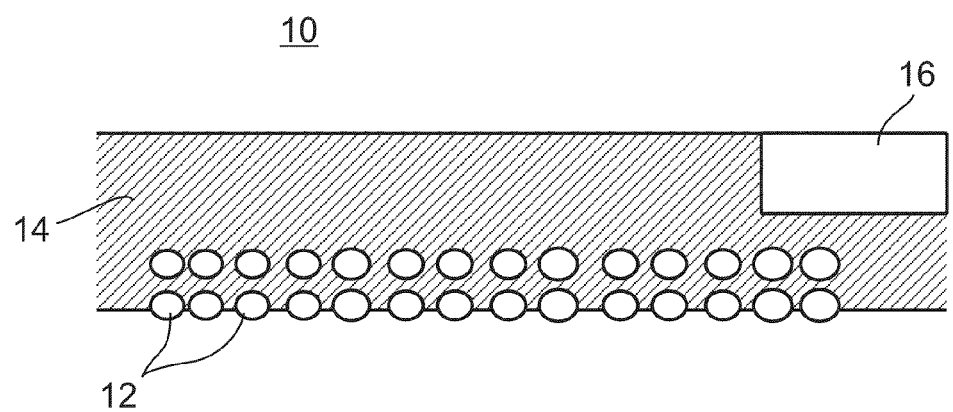
FIG. 2a is a schematic illustration of a delivery device according to the teachings of the present invention.

The present invention is of compositions, devices and methods utilizing stinging cells or capsules, which can be used, for example, for transdermal/intradermal, transmucosal or transcuticular delivery of an agent, such as for example a biologically active agent. Specifically, the present invention relates to the use of stinging cells (cnidocytes) or to stinging capsules isolated therefrom (cnidocysts) for transdermal/intradermal, transmucosal, transcuticular or transmembranal delivery of a therapeutic or a cosmetic agent.

The principles and operation of the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Throughout history man has exploited or imitated naturally occurring processes, e.g., biological processes, for the advancement of scientific fields such as medicine or engineering. As is further described herein, the present invention exploits the unique delivery mechanism of stinging cells, such as cnidocytes or isolated stinging capsules such as cnidocysts, for the delivery of therapeutic, diagnostic or cosmetic agents into tissues of a metazoan organism, such as, for example, a mammal.

By utilizing isolated stinging cells or capsules for delivery of an agent of choice, the present invention enables easy, efficient and painless delivery of a therapeutic or a cosmetic agents into, for example, mammalian tissues such as for example dermal tissues. The use of such stinging cells or capsules for delivery enables an accurate and localized delivery of precise dosages while being devoid of the pain and discomfort associated with other invasive delivery methods. In addition, by utilizing stinging cells or capsules for delivery, the present invention enables precise control over the depth of penetration and as such the tissue region of delivery. Tubules are capable of penetrating through tissue to a depth of up to 800 microns, depending on the tissue and stinging cell types from which they are discharged. As such, different stinging cell/capsule types can be utilized for delivery into different tissue regions or depths. For example, for tattoo injection, a stinging cell or capsule which can deliver the cosmetic dye into the area between the epidermis and the dermis is preferred.

It should be noted that unlike any other delivery devices currently in use, various types of stinging cells or capsules are able to efficiently and accurately deliver their contents directly into the epidermis. Currently, epidermal delivery of therapeutic compounds is generally effected by non specific diffusion which is slow and requires large concentrations of the therapeutic agent.

Thus, the efficiency and accuracy of the delivery device of the present invention makes it highly suitable for the treatment of, for example, psoriasis, where the depth of delivery is of crucial importance.

As used herein, the phrase "stinging cell" refers to the specialized cells (e.g. cnidocytes or nematocytes) present in, for example, all members of the phylum Cnidaria, Myxozoa, and Dinoflagellata. A stinging cell contains the "stinging capsule" which houses the delivery tubule.

The Cnidaria phylum represents about 10,000 species including sedentary single or colonial polyps and pelagic jellyfish, however only 15 species store and deliver compounds known to be irritating or toxic to mammals. In some animals cnidocytes consist for more than 45% of the cells present (Tardent 1995). There are at least three-dozen types of cnidae described in the literature including more than 30 varieties of nematocysts found in most Cnidaria and spirocysts and ptychocysts found mainly in the Cnidaria class Anthozoa (Mariscal 1974).

Although, cnidae are characteristic of Cnidaria they can be found in two other groups: the Myxozoa and the Dinoflagellata. Until recently Myxozoan were classified as a protozoa parasite however, based on phylogenetic analyses of 18S ribosomal RNA sequences it was suggested that the Myxozoa should be grouped in the metazoan phylum (Smothers et al. 1994). Anderson and Okamura (Anderson et al. 1998) placed the Myxozoa with the Bilateria, whereas Siddall et al. suggested that the Myxozoa belongs as a group to the Cnidaria phylum (Siddall et al. 1995). Myxozoan cnidae are very similar in their morphogenesis and mature structure to the Cnidarian cnidae. Formation of cnidae can be found in the protozoa Dinoflagellata, specifically in the colonial Dinoflagellate Polykrikos (Westfall et al. 1983). Polykrikos produces 2 distinct organelles: the nematocyst and the taeniocyst that are organized as a complex. The Polykrikos nematocyst (cnida) has a similar mature structure of Cnidarian cnida.

Thus, according to one aspect of the present invention there is provided a composition of matter, which includes a therapeutic agent such as a drug, antibody, protein, DNA construct and the like or a cosmetic agent such as a cosmetic dye, an anti-wrinkling agent, a vitamin, a skin peel agent, a hair follicle stimulating agent, a hair follicle suppressing agent and the like, and at least one stinging capsule.

The stinging capsule according to the teachings of the present invention can be an isolated stinging capsule or alternatively it can form a part of a stinging cell. In any case, the stinging capsule or cell is derived from an organism of the phylum Cnidaria, Myxozoa, or Dinoflagellata.

The stinging cell or capsule utilized by the present invention is preferably derived from an organism of the class Anthozoa, Hydrozoa or Scyphozoa. More specifically, the stinging cell/capsule utilized by the present invention can be derived from, for example, subclasses Hexacorallia or Octocorallia of the class Anthozoa, (mostly sea anemone and corals), subclasses Siponophora or Hydroida of the class Hydrozoa, or from subclasses Rhisostomeae or Semastomeae of the class Scyphozoa.

Stinging capsules from such organisms include toxins, which are non-toxic to humans, and other mammals. As such, these stinging cells or capsules isolated therefrom are ideally suited for safe and efficient delivery of a therapeutic or cosmetic agent into mammalian tissue.

It will be appreciated that the use of stinging cells from organisms which sequester toxins that are not fatal but cause only minor irritations to, for example, mammals, is also envisioned by the present invention.

In addition, stinging cells from other sources can also be utilized by the present invention provided inactivation of the endogenous toxin is effected prior to use.

Such inactivation can be effected via one of several methods, including but not limited to, temperature or chemical denaturation, enzymatic inactivation or ligand inactivation (e.g., Fab fragment of an antibody).

As is further described in the Examples section, which follows, toxins endogenous to cnidocysts can be efficiently and easily inactivated by incubating isolated cnidocysts at 45° C. for several hours. Alternatively, incubation at a high temperature of 70-95° C. for several minutes can also be utilized by the present invention.

As demonstrated herein, incubation of cnidocysts at 45° C. for 22 hours does not damage or trigger activation of the cnidocyst. Such conditions are effective in denaturing polypeptides stored within the cnidocyst, such as the polypeptide toxins and enzymes delivered by the tubule of the cnidocyst. It will be appreciated that since organisms of, for example, the phylum Cnidaria habitat aquatic environments, which are characterized by temperatures well below 30° C., polypeptides stored within their stinging capsules can be denatured via incubation in temperatures well above 30° C.

The stinging cell or the stinging capsule of the present invention can be isolated from a cell extract prepared from organs or parts of an organism, which contain the stinging cells (for example a whole hydra or tentacles). Alternatively, stem cells, which give rise to cnidocytes or cnidocysts, can be isolated and cultured or utilized directly. It will be appreciated that the composition of matter of the present invention can also directly utilize the organs, tentacles, or parts of an organism, and the whole organism (hydra for example), which contain the stinging cells without the need for isolating individual stinging cells or for isolating the capsules from the cells.

Thus, according to the teachings of the present invention isolated and optionally pretreated stinging cells or stinging capsules can be utilized for delivering a therapeutic or cosmetic agent into a tissue region of an individual. Preparation of such delivery devices is described in detail in Examples 1 and 3 of the Examples section, which follows.

Delivery of a therapeutic or cosmetic agent according to the present invention can be effected by applying the composition of matter described above to an outer surface of the tissue (e.g., skin). Following application, the stinging cells or the isolated capsules are triggered (as is further described hereinbelow) and the therapeutic or the cosmetic agent is thereby delivered by the tubule into the tissue.

Alternatively, the therapeutic or cosmetic agent can be applied onto the outer surface of the tissue, followed by application of stinging cell(s) or stinging capsules to the same region. Upon triggering, the agent is pumped into the stinging cells or into the capsules (as is further described herein) and the therapeutic or the cosmetic agent is delivered via the tubule into the tissue.

According to preferred embodiments of the present invention, the therapeutic agent can be any biological active factor such as, for example, a drug, a nucleic acid construct, a vaccine, a hormone, an enzyme, small molecules such as for example iodine or an antibody. Examples include, but are not limited to, antibiotic agents, free radical generating agents, anti fungal agents, anti-viral agents, non-nucleoside reverse transcriptase inhibitors, protease inhibitors, non-steroidal anti inflammatory drugs, immunosuppressants, anti-histamine agents, retinoid agents, tar agents, anti-puritic agents, hormones, psoralen, and scabicide agents. Nucleic acid constructs deliverable by the present invention can encode polypeptides (such as enzymes ligands or peptide drugs), antisense RNA, or ribozymes.

The therapeutic agent can also be a prodrug, which is activatable prior to, during, or following discharge of the stinging capsule. As used herein in the specification and in the claims section which follows, the term "prodrug" refers to an agent which is inactive but which is convertible into an active form via enzymatic, chemical or physical activators.

A prodrug (for example an enzyme) can be activated just prior to stinging cell discharge by providing an activator compound (for example an ion), which can be diffused or pumped (during discharge) into the capsule. Alternatively, specific enzymes, molecules or pH conditions present in the target tissues, can activate the prodrug.

The cosmetic agent of the present invention can be, for example, an anti-wrinkling agent, an anti-acne agent, a vitamin, a skin peel agent, a hair follicle stimulating agent or a hair follicle suppressing agent. Using the stinging cells/capsules of the present invention a more effective delivery of such cosmetic agents can be effected. Examples of cosmetic agents include, but are not limited to, retinoic acid and its derivatives, salicylic acid and derivatives thereof, sulfur-containing D and L amino acids and their derivatives and salts, particularly the N-acetyl derivatives, alpha-hydroxy acids, e.g., glycolic acid, and lactic acid, phytic acid, lipoic acid and many other agents which are known in the art, such as, for example the hair follicle stimulating or suppressing agents described hereinbelow.

In addition, stinging cells or isolated capsules injecting a cosmetic dye can be utilized as a sterile, needle free and pain free method of producing permanent or transient tattoos. For such purposes, a predetermined pattern of stinging cells/capsules can be attached to a support such as a plaster, foil or the like as described hereinabove. The stinging cells/capsules can be preloaded with a cosmetic dye or immersed therein prior to, or during triggering activation (e.g., the cosmetic dye can be applied to the skin). Upon stinging cells/capsules discharge (via, for example, skin contact), the dye would penetrate into the skin to form a predetermined dye pattern (tattoo).

According to one preferred embodiment of the present invention, the therapeutic or cosmetic agent is disposed within the liquid stored in the stinging cell or the stinging capsule. In such a case, the stinging cell or the isolated capsule is loaded with the therapeutic or cosmetic agent via any one of several methods generally known in the art such as, but not limited to, diffusion, electroporation, liposome fusion, microinjection and the like.

Alternatively and according to another preferred embodiment of the present invention, the therapeutic or cosmetic agent is disposed in a liquid surrounding the stinging cell or the isolated capsule. In such a case, the stinging capsule's natural mechanism of osmotically collecting liquid from the environment following triggering (further detailed in the background section hereinabove) pumps the therapeutic or cosmetic agent into the stinging cell just prior to or during the discharge.

In any case, since a stinging capsule is highly permeable to water and molecules, therapeutic or cosmetic agent loading prior to or during discharge can be easily achieved.

As is further described in Example 4 of the Examples section, which follows, a pigment disposed in water surrounding an isolated stinging capsule easily penetrates the capsule via simple diffusion and thus can be discharged following activation.

Prior art studies which concentrated on deciphering the permeability and functionality of stinging capsules have shown that alkali ions, monovalent ions, divalent ions, or small organic cations such as Tris+ or choline+, penetrate cnidocysts and accumulate inside without affecting the properties of the stinging cell or capsule. Studies performed by Lubbock & Amos in order to understand the effect of calcium on capsule discharge (1981) have shown that in the predischarged state the cnida wall is permeable to water and to charged molecules of relatively low molecular weight like bromophenol blue (MW 670) and fluoresceinate (MW 376). Hidaka, who investigated of the mechanism of capsule discharge (1992, 1993) demonstrated that cnidocysts stained with toluidine blue (MW 306) released the blue stain through the tubule when discharged leaving the capsule completely clear. Heeger et al., (1992) investigated the ability of different commercially available lotions to protect human skin against stinging cell penetration.

Thus, short polypeptides, hormones, or any low molecule weight agents can be loaded into stinging cells through simple diffusion. These active compounds can be stored in the stinging capsule and injected into the target tissue upon discharge.

As mentioned hereinabove, during the discharge process, the immediate liquid surrounding the stinging cell is pumped into the capsule and than injected via the tubule. Since the surrounding liquid is pumped into the cnida under extremely high pressures over a short period of time it is highly plausible that high molecular weight molecules, such as polypeptides polynucleotides and other complex molecules can penetrate the capsule and be delivered via the tubule upon discharge.

In any case, the composition of matter described above can be directly utilized to deliver the therapeutic or cosmetic agent into mammalian and other tissue by applying the stinging cells or capsules isolated therefrom, which include the agent, or by co-applying the agent and stinging cell/capsule onto a skin region of an individual (e.g. a human or livestock and other) and triggering discharge either automatically (via contact with the tissue) or manually via an activation mechanism which is described in detail hereinbelow.

Triggering the activation of the stinging cell/capsules thus leads to the subsequent transdermal/intradermal, transmucosal, transmembranal or transcuticular delivery of the therapeutic or cosmetic agent.

To stabilize the therapeutic or cosmetic agent and/or the stinging cell(s)/capsule(s) and to possibly enhance triggering efficiency, the composition of matter of the present invention is preferably included in a pharmaceutical composition.

Thus, according to another aspect of the present invention there is provided a pharmaceutical composition, which includes, as an active ingredient, a therapeutic or cosmetic agent, at least one stinging capsule (either isolated or forming a part of a stinging cell) and a pharmaceutically acceptable carrier.

Hereinafter, the phrase "pharmaceutically acceptable carrier" refers to a carrier, which does not cause significant irritation to the individual treated and does not abrogate the biological activity and properties of the active ingredient. Preferably, the pharmaceutically acceptable carrier does not affect the ability of the stinging cells to discharge following triggering although in some instances, a pharmaceutically acceptable carrier which inhibits triggering mediated by tissue contact can also be utilized by the present invention.

The pharmaceutical composition of the present invention includes a pharmaceutically acceptable carrier, which is formulated for topical, transmucosal or transnasal applications.

For topical application, the active ingredient and stinging cell(s)/capsule(s) may be suspended in hydrophilic or hydrophobic-based carrier such as a gel suitable for topical applications.

For topical, transmucosal or transnasal administration, the active ingredient and stinging cells can be conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount.

In any case, application of the composition to, for example, a skin region leads to subsequent contact between the stinging cell(s)/capsule(s) and the skin the individual which contact triggers discharge of the stinging cell/capsule and delivery of the active ingredient into for example, an epidermis or dermis tissue region of the individual.

Although, for some applications, contact mediated discharge suffices, such activation can be inefficient since it enables discharge of only the portion of stinging cells, which come into physical contact with the tissue following application.

To enable a more efficient and consistent discharge and thus delivery of the active agent, the pharmaceutical composition of the present invention can include a pharmaceutically acceptable carrier which inhibits discharge of the stinging cell(s)/capsule(s) upon tissue contact (e.g., skin contact). In such cases, the pharmaceutical composition also includes a chemical activator, such as, for example NaSCN or EGTA, which can be applied prior to, or following, application of the pharmaceutical composition and which triggers discharge of the stinging cells. Chemical or electrical activation of discharge is advantageous since it allows for simultaneous discharge of most if not all of the stinging cells of the pharmaceutical composition.

According to the teachings of the present invention, the stinging cells/capsules described above can also be utilized in a delivery device useful for delivering a therapeutic or cosmetic agent into a tissue region of an individual.

Thus, as specifically shown in FIG. 2a and according to yet another aspect of the present invention there is provided a delivery device, which is referred to herein as device 10.

Device 10 includes at least one stinging cell/capsule 12 (several are shown). Upon discharge, stinging cell/capsule 12 is capable of delivering (via it's tubule) liquid disposed in or around stinging cell/capsule 12 into a tissue region (as described hereinabove). Device 10 further includes a support 14, which serves for supporting stinging cell/capsule 12 and for applying stinging cell/capsule 12 to an outer surface of the tissue region into which delivery is desired.

Device 10 can be utilized to deliver a therapeutic or a cosmetic agent, which is loaded into stinging cell(s)/capsule(s) 12 or disposed in a liquid surrounding stinging cell(s)/capsule(s) 12.

Support 14 can be, for example, a patch, a foil, a plaster or a film or any material capable of supporting stinging cell(s)/capsule(s) 12 in a manner suitable for application to, for example, a skin region of the individual.

Stinging cells 12 can be secured to support 14 via, for example, biological glue (e.g. BIOBOND™), polylysine, a mesh support or the like.

Discharge of stinging cell(s)/capsule(s) 12 can be activated upon contact with tissue as described above. For example, following application of device 10, pressure can be exerted on support 14 thus forcing contact between stinging cells 12 and the tissue region thereby activating discharge. Alternatively, discharge can be activated by a mechanism 16 included within device 10.

Mechanism 16 can be an electrical or chemical activating mechanism which when activated by a physician or by the individual to be treated, triggers simultaneous discharge of stinging cell(s)/capsule(s) 12 preferably in a rapid and uniform manner.

Figure 2B:
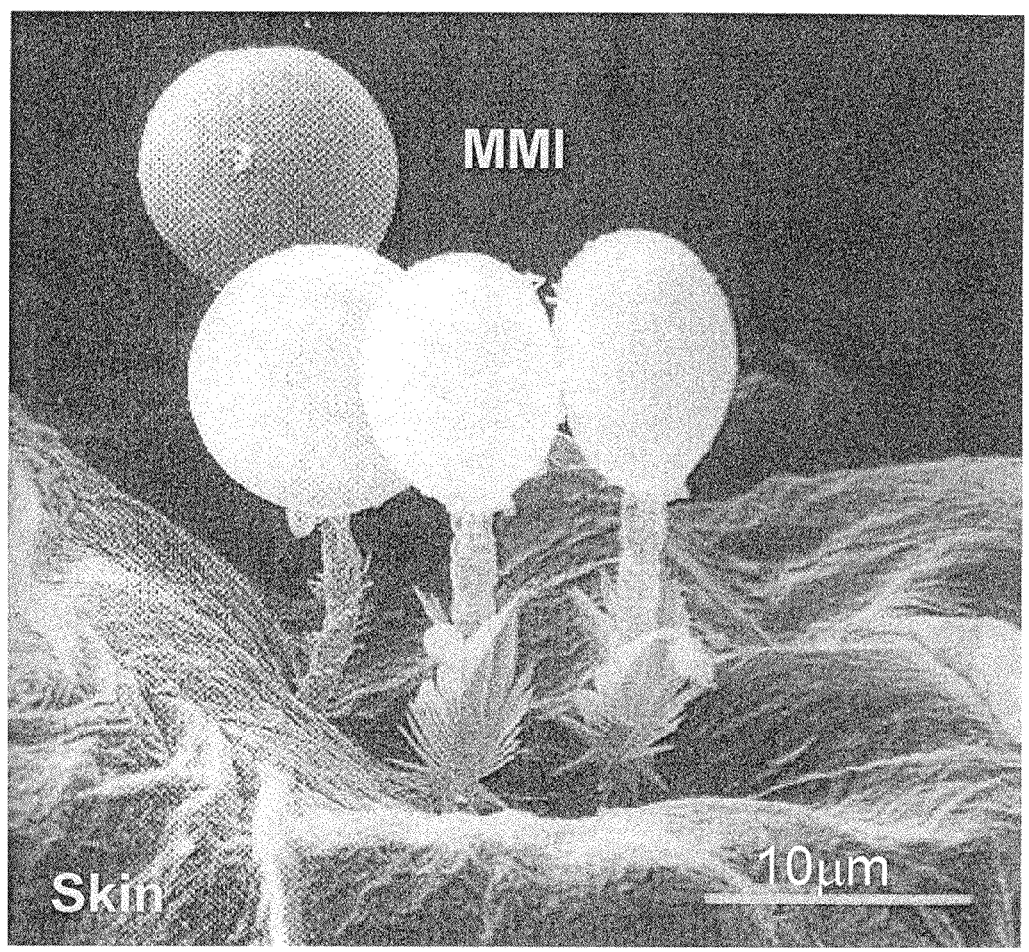
FIG. 2b is a prior art scanning electron micrograph showing stinging cells of *Cyanea capillata* following activation via human skin contact.

Chemical triggering can be mediated by substances such as free and conjugated N-acetylated sugars or low molecular weight amino compounds which are known to be detected by at least two classes of stinging cell chemoreceptors. FIG. 2b shows a prior art image of stinging capsules isolated from *Cyanea capillata* following activation by contacting human skin.

As is further described in Example 2 of the Examples section below, Sodium thiocyanate (NaSCN) is capable of triggering discharge of cnidocysts. In addition, Lubbock and Amos (1981) have shown that isolated cnida (cnidocysts) can discharge normally when placed in buffered EGTA or 10 mM citrate solution; Weber (1989) demonstrated the effect of dithioerthritol or proteases on discharging isolated cnida and Hidaka (1993) discussed various agents which can trigger cnida discharge.

Electrical triggering can be achieved via an electrical pulse of 30 microseconds of approximately 20-30 Volts as is further described in the literature (Holstein and Tardent 1984; Tardent and Holstein 1982).

As mentioned hereinabove, the present invention can be utilized to deliver a variety of therapeutic agents. Such therapeutic agents combined with the effective delivery obtainable via stinging cells/capsules can be utilized to treat a variety of disorders.

An example of a very common skin infection is acne, which involve infestation of the sebaceous gland with p. acnes, as well *Staphylococcus aurus* and *pseudomonas*. The disorder can be treated by anti-bacterial agents such as phenols, including cresols and resorcinols and antibiotics such as chloramphenicol, tetracyclines, synthetic and semi-synthetic penicillins, beta-lactames, quinolones, fluoroquinolines, macrolide antibiotics, peptide antibiotics, cyclosporines, erytromycin and clindamycin.

Psoriasis, which is a common skin disorder can be treated by using the present invention for accurate and efficient intraepidermal delivery of steroidal anti-inflammatory agents or other known drugs with limited skin permeability.

Fungal infections can also be treated via the pharmaceutical composition or delivery device of the present invention. Superficial fungal infection of the skin is one of the commonest skin diseases seen in general practice. Dermatophytosis is probably the most common superficial fungal infection of the skin. Candidiasis is an infection caused by the yeast like fungus *candida albicans* or occasionally other species of *candida*. Antifungal drugs, which are active against dermatophytes and *candida* such as azoles, diazoles, triazoles, miconazole, fluconazole, ketoconazole, clotrimazole, itraconazole griseofulvin, ciclopirox, amorolfine, terbinafine, Amphotericin B, potassium iodide, flucytosine (5FC) and any combination thereof at a therapeutically effective concentration can be delivered intraepidermally via the delivery device or method of the present invention.

The present invention can be also used for delivering pigments, such as photosensitizers utilizable in photo dynamic therapy (PDT), into cells of skin cancer or other skin disorders. Photosensitizers are chemical compound which produce a biological effect upon photoactivation, or a biological precursor of a compound that produces a biological effect upon photoactivation. Examples of photosensitizers which can be delivered by the stinging cells/capsules of the present invention include, but are not limited to, hematoporphyrins (Batlle 1993 J. Photochem. Photobiol. Biol. 20:5-22 and Kessel 1988 Cancer Let. 39:193-198), uroporphyrins and phthalocyanines (Kreimer-Birnbaum, 1989 Seminars in Hematology 26:157-173), purpurins (Morgan et al. 1990 Photochem. Photobiol. 51:589-592 and Kessel, 1989 Photochem. Photobiol. 50:169-174), acridine dyes and bacteriochlorophylls (Beems et al. 1987 Photochem. Photobiol. 46:639-643 and Kessel et al. 1989 Photochem. Photobiol. 49:157-160), and bacteriochlorins (Gurinovich et al. 1992 J. Photochem. Photobiol. Biol. 13:51-57).

By enabling accurate and efficient delivery of photosensitizers, the present invention substantially improves the efficiency of PDT.

Eye infections such as conjuctivitis, caused by bacteria such as *staphylococcus aureus, streptococcus pneumoniae*, and *haemophilus influenzae* can be treated with antibiotic ointments, e.g., bacitracin which is delivered via the delivery device or method of the present invention.

Chronic rheumatic or arthritic conditions are usually treated by NSAIDs. Such as salicylic acid, or aspirin, and ibuprofen are well-known examples of NSAI drugs. Patients taking NSAIDs drugs orally face an increased risk for peptic ulcers and gastrointestinal blood loss resulting in anaemia. Such adverse reactions especially plague patients taking NSAIDs drugs over prolonged periods. Transdermal administration of NSAIDs via the delivery device or method of the present invention will prevent the gastrointestinal complications. Transdermal drug delivery according to the present invention provides other benefits such as less frequent dosing; better controlled drug release, and a greater ability to target delivery to specific tissue sites.

Anaesthetics can be used for alleviating pain for example during suturing, or in infections, which are accompanied with pain sensation. Examples of topical anaesthetic drugs include without limitation benzocaine, lidocaine, bupivacaine, chlorprocaine, dibucaine, etidocaine, mepivacaine, tetracaine, dyclonine, hexylcaine, procaine, cocaine, ketamine, pramoxine, phenol, and pharmaceutically acceptable salts thereof all of which are deliverable via the delivery device or method of the present invention.

The stinging capsules or cells of the present invention can be used to treat hair loss, excessive hair growth, or discoloration of the hair.

For example, a hair follicle stimulating agent such as hinokitiol, or pantothenic acid can be delivered by the stinging cells/capsules of the present invention directly into the follicle in order to stimulate hair growth.

Alternatively, the stinging cells/capsules of the present invention can be utilized to deliver, directly into hair follicles, a hair follicle suppressing agent capable of suppressing hair growth. Examples of agents capable of suppressing hair growth include, but are not limited to, non-steroidal suppressors of angiogenesis and inhibitors of 5-alpha reductase, ornithine decarboxylase, S-adenosylmethionine decarboxylase, gamma-glutamyl transpeptidase, and transglutaminase.

The present invention can also be utilized to pigment hair color by delivering, for example, melanin or tyrosinase, into the hair follicle.

In addition to the above, the teachings of the present invention can also be utilized to deliver drugs into blood circulation via either transdermal delivery, which leads to diffusion into small capillaries or by applying the delivery device of the present invention to internal body tissues.

In such cases, the present invention can be utilized to deliver drugs such as hormones (e.g., insulin), antibiotics, cardiac drugs and the like.

The stinging cells/capsules of the present invention can also be utilized for vaccination. Vaccine antigens can be delivered to specialized immune cells underlying the skin or into blood circulation (as described above).

Absorption into the blood stream following transdermal delivery will most likely result in transport of the antigen to the phagocytic cells of the liver, spleen, and bone marrow. Since such cells serve as antigen presenting cells, a strong immunogenic response will be elicited leading to effective immunization.

Thus, the present invention overcomes the limitations of prior art devices and methods while providing a safe, efficient and contamination risk free method for delivering agents across epidermal mucousal or membranal barriers.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions illustrate the invention in a non-limiting fashion.

Example 1

Isolation of Capsules

Fresh tentacles of *Rhopilema nomadica* were homogenized in seawater. 300 l of the homogenate was added to 300 l Percoll in a microfuge tube. The tube was shaken over ice for 30 min and then centrifuged for 10 minutes, at 1000 rpm. The pellet was washed 3 times with $H_2 0$ and resuspended in 50 l $H_2 0$. The tube was kept at 4° C. until use.

Example 2

Discharging the Capsules

Figure 3:
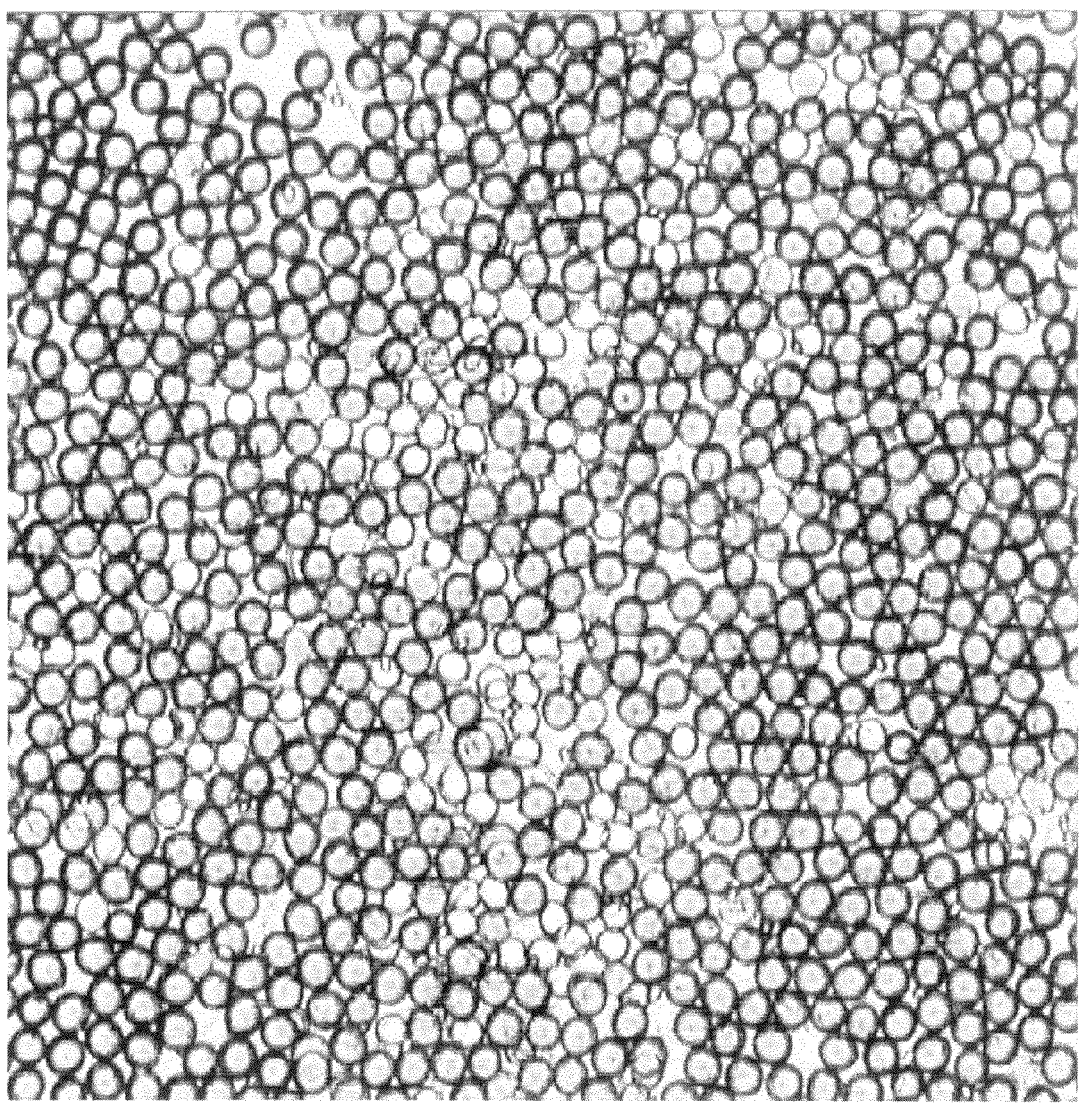
FIG. 3 is a microscope image of capsules (stinging capsules) isolated from *Rhopilema nomadica* tentacles.
Figure 4:
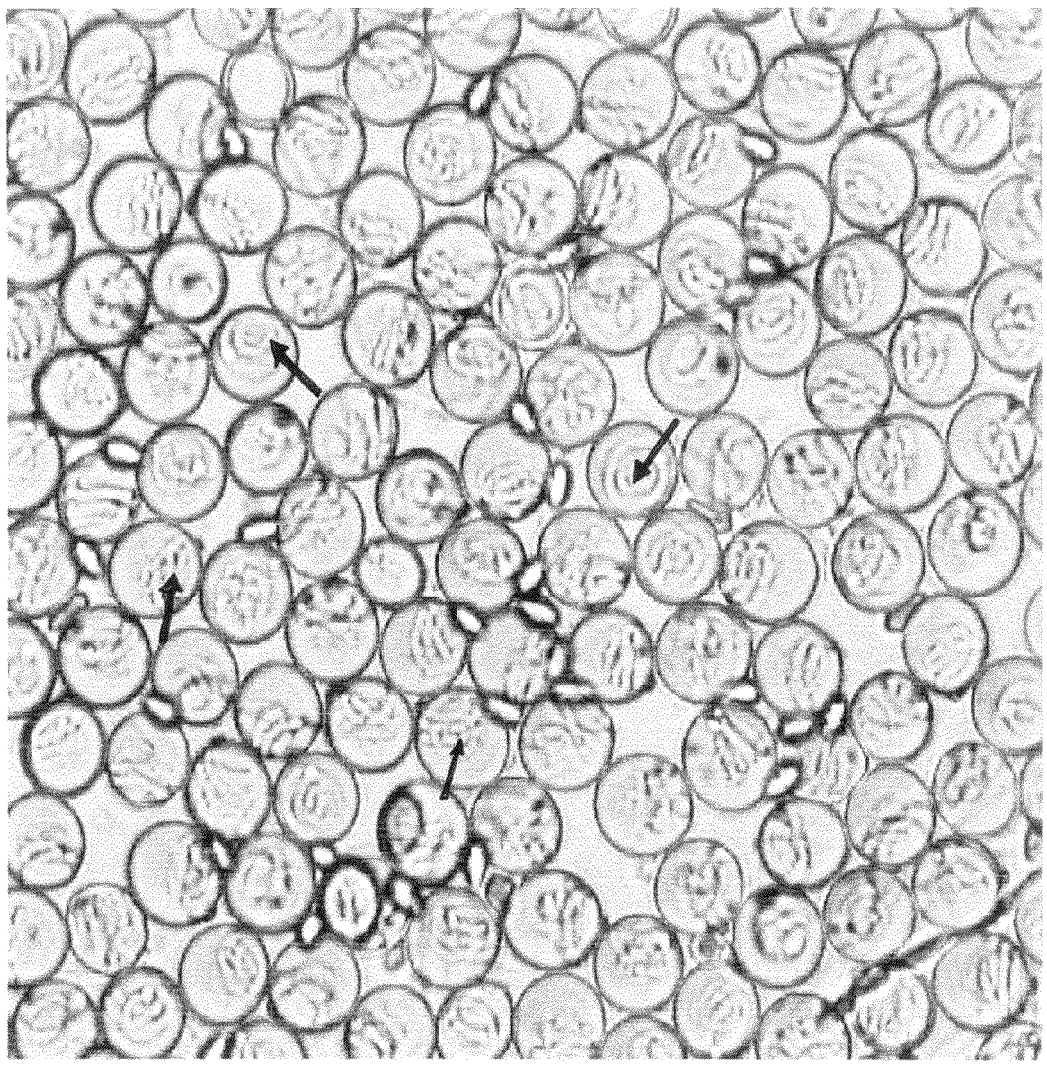
FIG. 4 is a microscope image of capsules isolated from *Rhopilema nomadica* tentacles. The folded tubule inside some of the capsules is marked with an arrow.
Figure 5:
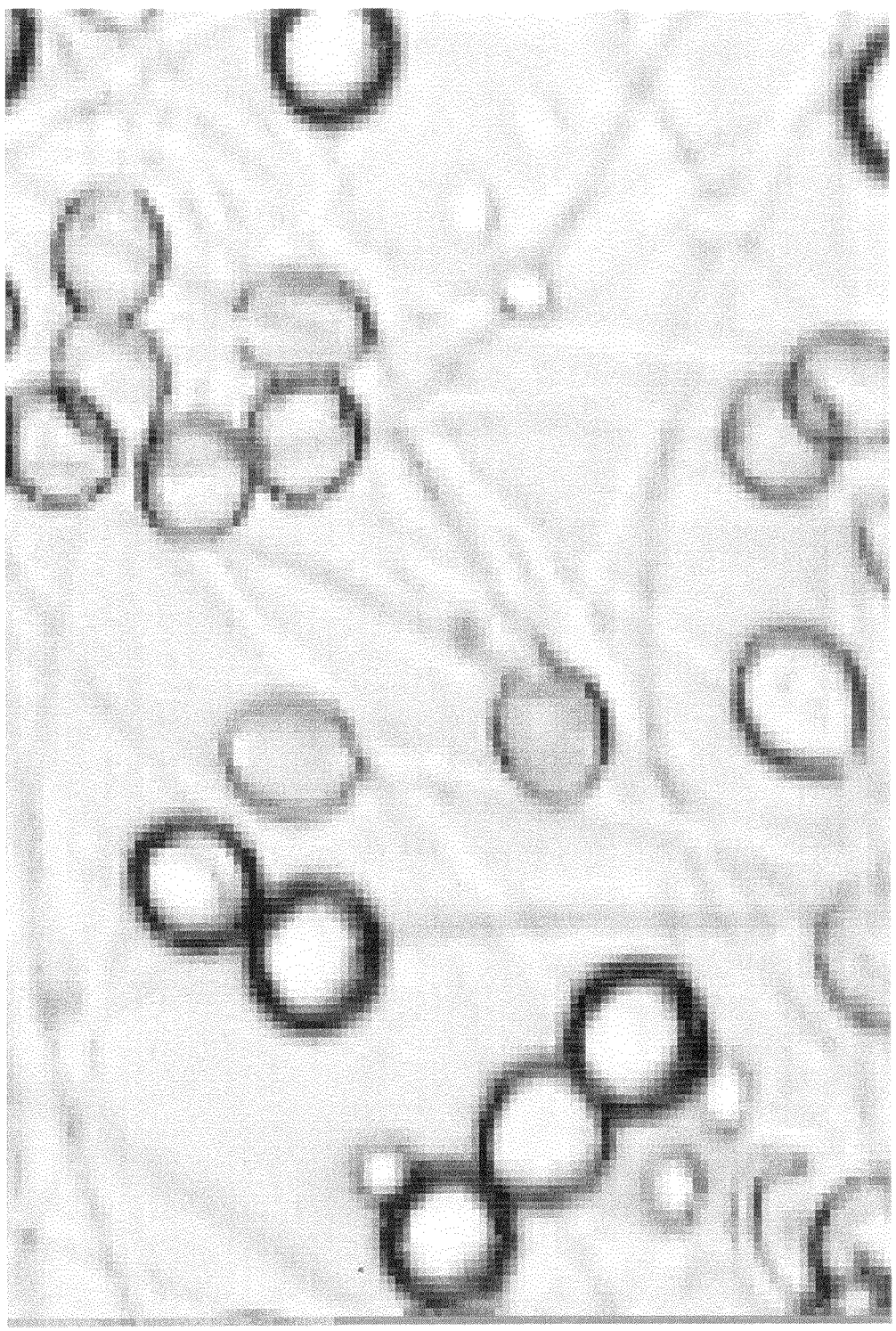
FIG. 5 is a microscope image of capsules isolated from *Rhopilema nomadica* following discharge activation with NaSCN.

A 2 l sample of the above-described preparate was applied to a microscopic slide, and the isolated capsules were photographed under a light microscope (Leitz Laborlux S) (See FIG. 3 and FIG. 4). Two l of Sodium thiocyanate were added to the isolated capsules. Following the NaSCN administration capsules immediately discharged to release their tubules. The discharged capsules were photographed under a light microscope (FIG. 5).

Example 3

Inactivation of Capsule-Stored Polypeptides

The temperature range, which is tolerated by *Rhopilema nomadica*, is between 16° C.-30° C. Therefore, it is possible to perform denaturation and inactivation of an endogenous polypeptide at 45° C. Isolated capsules were incubated for 22 hours in 45° C. Following the heat inactivation process the capsules were intact and their round shape was unchanged. Moreover, the heated capsules were able to discharge normally upon treatment with NaSCN.

Example 4

Altering the Content of the Isolated Capsules

Figure 6:
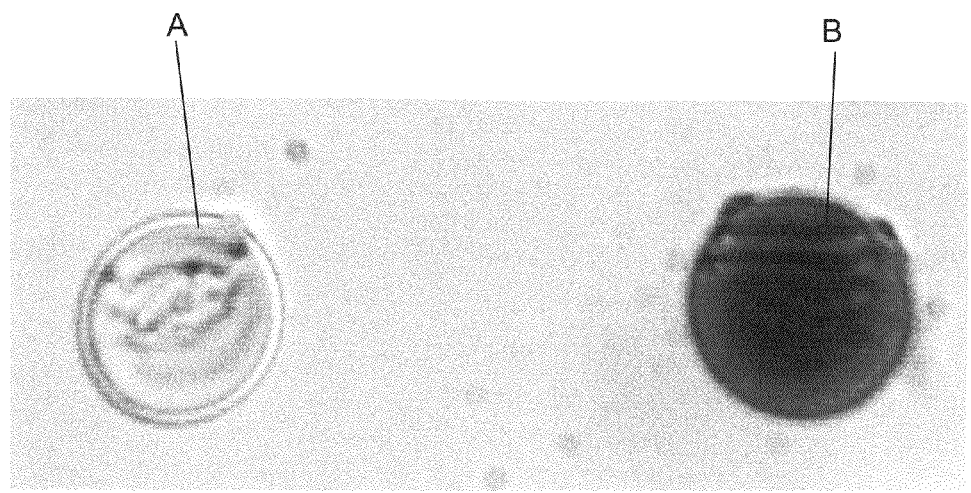
FIG. 6 illustrates capsules isolated from *Rhopilema nomadica* (Arrow B) and loaded with a pigment (arrow A)
Figure 7:
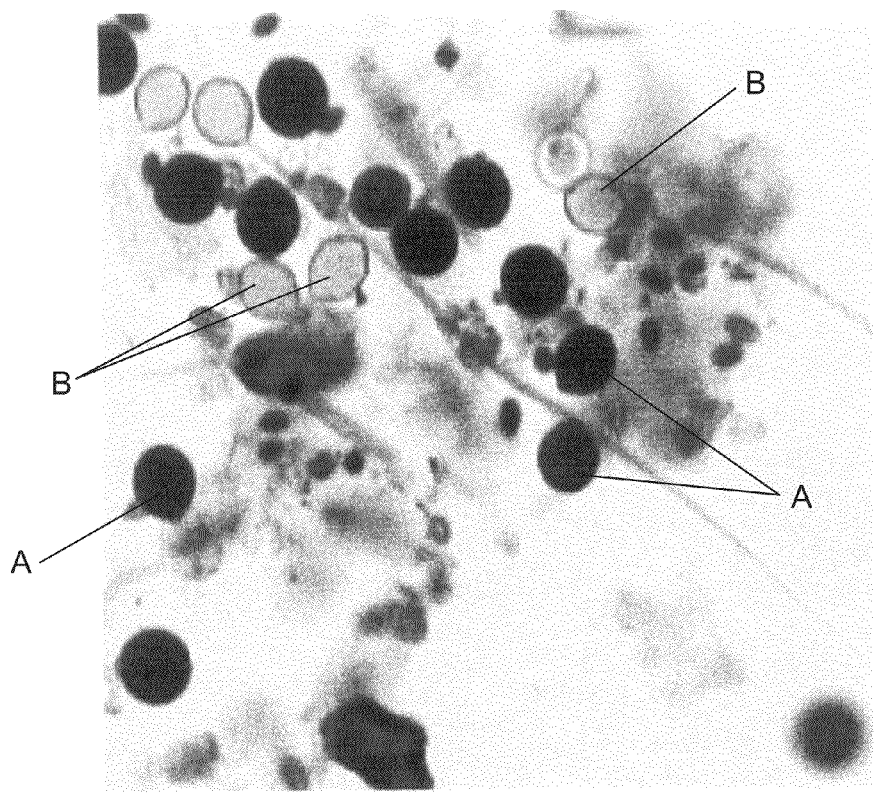
FIG. 7 illustrates capsules isolated from *Rhopilema nomadica* and loaded with a pigment of a molecular weight of 306 daltons, prior to (arrow A) and following (arrow B) discharge activation with NaSCN.
Figure 8:
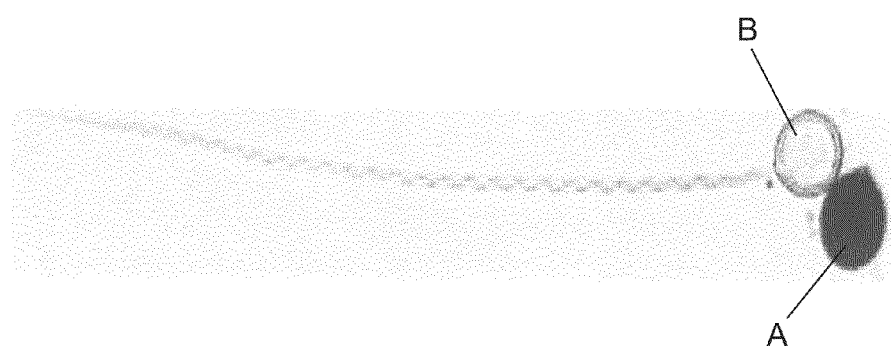
FIG. 8 illustrates capsules isolated from *Rhopilema nomadica* and loaded with a pigment of a molecular weight of 306 daltons, prior to (arrow A) and following (arrow B) discharge activation with NaSCN.

Isolated capsules were treated with 0.1% Toluidine Blue O for 3 minutes and than washed 3 times with $H_2 0$. The pigment penetrated the intact capsules and the stained capsules were photographed (FIGS. 6-8, A arrow). Upon activation with NaSCN the capsules containing the pigment discharged normally and released the pigment through the tubule to the surrounding solution (FIGS. 7-8, B arrow).

Figure 9:
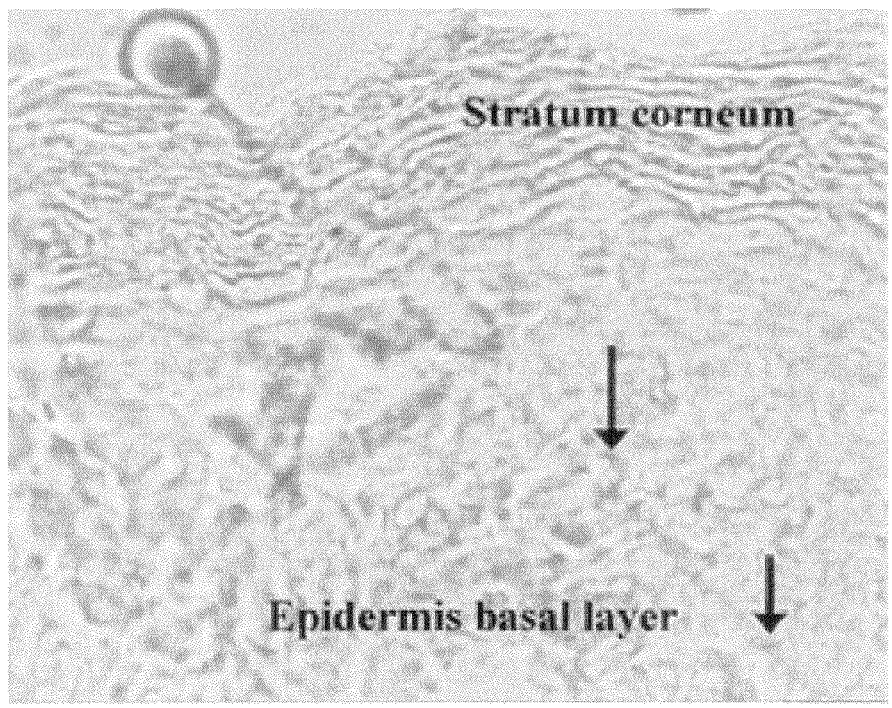
FIG. 9 illustrates dermal penetration of a tubule discharged from an isolated cnidocyst (tubule indicated by arrows)
Figure 10:
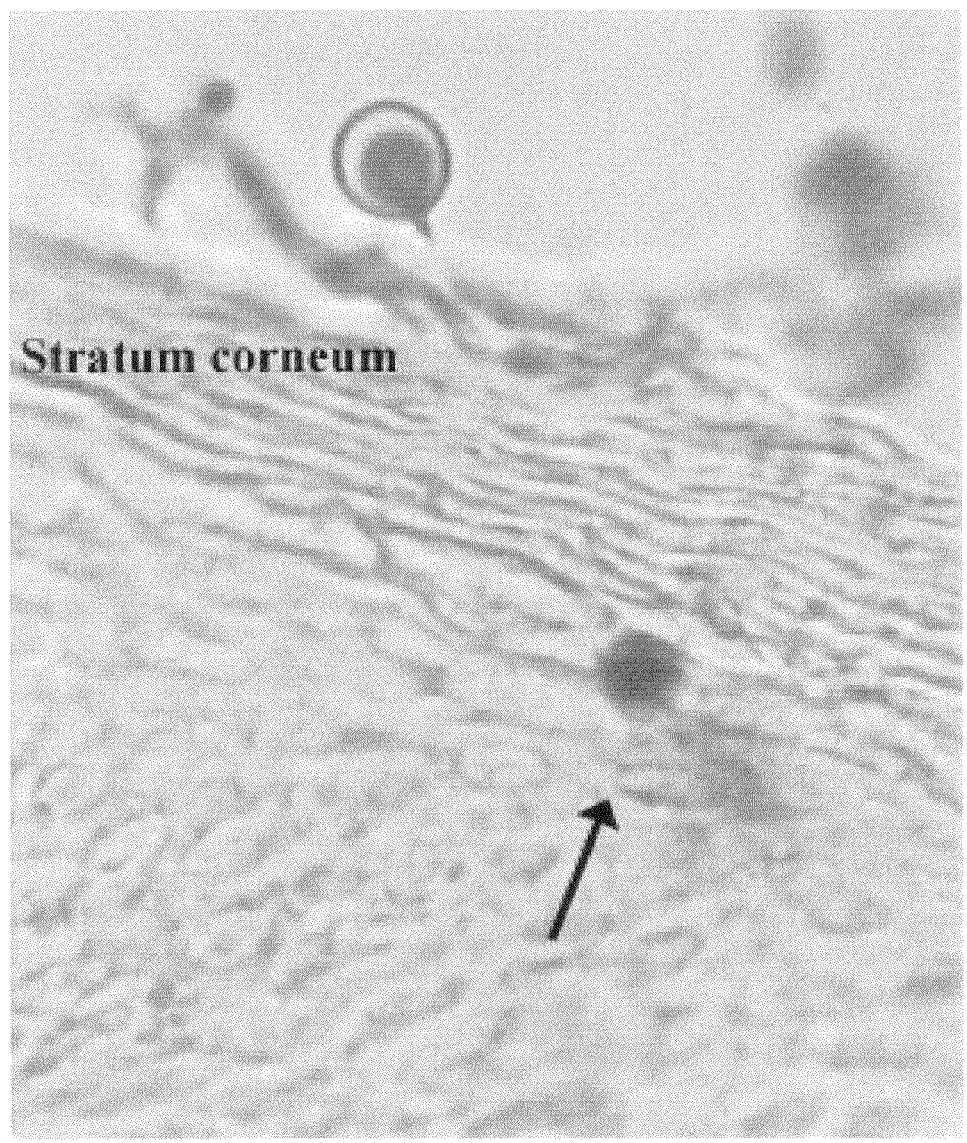
FIG. 10 illustrates an intraepidermal injection of a pigment (306 daltons) via a preloaded cnidocyst (arrow indicates region of delivery).

To demonstrate intraepidermal penetration of the delivery tubule, capsules isolated from *Rhopilema nomadica* were loaded with a pigment (0.1% Toluidine Blue O, MW—306 daltons) and discharged using NaSCN. As specifically shown in FIG. 10, which depicts an experiment performed on a 15 micron thick human skin section, following discharge, the tubule penetrated the stratum corneum and delivered the pigment stored by the capsule into the squamous cell layer of the epidermis. The tubule penetration path is depicted in more detail in FIG. 9.

Example 5

Drug Delivery Using Stinging Capsules—Theoretical Considerations

Psoralen:

Psoralen photochemotherapy [psoralen ultraviolet A (PUVA)] plays an important role in dermatological therapeutics, and is utilized for treating psoriasis and other dermatoses.

The oral recommended dose for psoralen is approximately 0.5 mg/kg weight. Peak plasma concentration following oral administration varies from 2 nanograms/ml to 167 nanograms/ml (mean 56 nanograms/ml).

As detailed hereinunder, the present invention can be utilized to deliver psoralen in an efficient and accurate manner.

Since hydra cnidocysts are spherical in shape, with a diameter of approximately 10 micrometers, their volume can be calculated as $4/3 \times \pi \times r^3 \sim 4 \times 5^3 = 500 \, \mu m^3$ When filled, the capsule contains approximately 0.5 nanograms of water. Since a loaded drug, such as psoralen, can occupy 5-10% of the capsule volume, a single loaded capsule contains about 0.05 nanograms of the drug. Since $2 \times 10^4$ to $10^6$ cnidocysts can penetrate a 1 cm² region of skin, the amount of drug which can be delivered by capsules into 1 cm² of skin is: 0.05 nanograms of the drug$\times 2 \times 10^4$ to $10^6$ cnidocysts which equal to 1-50 μg of the drug per 1 cm² of skin, which is 20-1000 fold higher than the amount deliverable by oral administration. Thus, the present invention can provide targeted delivery of psoralen at high concentrations while at the same time not inducing toxicity in other tissues of the body.

Viagra:

Recently, a new drug was developed to treat male erectile dysfunction: sildenafil citrate (Viagra). The recommended doses for oral administration for this drug is 25-100 mg once a day. Maximal plasma concentration of 440 ng/ml, are reached within 30 to 120 minutes following oral administration of 100 mg.

Using the above described calculations for stinging cells/capsules, targeted delivery of higher concentrations of sildenafil citrate can be effected.

Diphenhydramine Hydrochloride:

Diphenhydramine hydrochloride is an antihistamine used in the treatment of allergies, stings and skin irritations. An oral dose of 120 mg/kg results in a peak plasma concentration of 0.2 g/ml.

2 hours following administration. Although the same drug can be administered topically by the application of 1-2% diphenhydramine hydrochloride this pharmaceutical formulation is known to have low penetration and thus a slow therapeutic effect.

Thus, the teachings of the present invention can provide an efficient, rapid and targeted delivery of drugs to treated tissues.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications disclosed therein and/or mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

REFERENCES

1. Anderson, C. L., Canning, E. U., and Okamura, B. (1998). "A triploblast origin for Myxozoa?" *Nature,* 392(6674), 346-7.
2. Brennecke, T., Gellner, K., and Bosch, T. C. (1998). "The lack of a stress response in Hydra oligactis is due to reduced hsp70 mRNA stability." *Eur J Biochem,* 255(3), 703-9.
3. Godknecht, A., and Tardent, P. (1988). "Discharge and mode of action of the tentacular nematocysts of *Anemonia sulcata* (Antozoa: Cnidaria)." *Marine Biology,* 100, 83-92.
4. Heeger, T., Moller, H., and Mroweitz, U. (1992). "Protection of human skin against jellyfish (*Cyanea capillata*) stings." *Marine Biology,* 113, 669-678.
5. Hidaka, M. (1992). "Effects of Ca+ on the volume of nematocysts isolated from acontia of the sea anemone *Calliactis tricolor.*" *Comp Biochem Physiol,* 101A(4), 737-741.
6. Hidaka, M. (1993). "Mechanism of nematocystn discharge and its cellular control." *Advances in Comparative and Environmental Physiology,* 15, 45-76.
7. Holstein, T., and Tardent, P. (1984). "An ultrahigh-speed analysis of exocytosis: nematocyst discharge." *Science,* 223(4638), 830-3.
8. Lotan, A., Fishman, L., Loya, Y., and Zlotkin, E. (1995). "Delivery of a nematocyst toxin *Nature,* 375(6531), 456.
9. Lotan, A., Fishman, L., and Zlotkin, E. (1996). "Toxin compartmentation and delivery in the Cnidaria: the nematocyst's tubule as a multiheaded poisonous arrow." *J Exp Zool,* 275(6), 444-51.
10. Lubbock, R. (1979). "Chemical recognition and nematocyte excitation in sea anemone." *J. exp. Biol.,* 83, 283-292.
11. Lubbock, R., and Amos, W. B. (1981). "Removal of bound calcium from nematocyst contents causes discharge." *Nature,* 290(5806), 500-1.
12. Mariscal, R. N. (1974). *Coelenterate biology: reviews and new perspectives,* Academic Press, New York.
13. Siddall, M. E., Martin, D. S., Bridge, D., Desser, S. S., and Cone, D. K. (1995). "The demise of a phylum of protists: phylogeny of Myxozoa and other parasitic cnidaria." *J Parasitol,* 81(6), 961-7.
14. Smothers, J. F., von Dohlen, C. D., Smith, L. H., Jr., and Spall, R. D. (1994). "Molecular evidence that the myxozoan protists are metazoans." *Science,* 265(5179), 1719-21.
15. Tardent, P. (1995). "The cnidarian cnidocyte, a high-tech cellular weaponry." *BioEssays,* 17(4), 351-362.

16. Tardent, P., and Holstein, T. (1982). "Morphology and morphodynamics of the stenotele nematocyst of Hydra attenuata Pall. (Hydrozoa, Cnidaria)." *Cell Tissue Res,* 224 (2), 269-90.
17. Thorington, G. U., and Hessinger, D. A. (1988). "Control of cnida discharge: I. evidence for two classes of chemoreceptor." *Biol. Bull.,* 174, 163-171.
18. Watson, G. M., and Hessinger, D. (1989). "Cnidocyte mechanoreceptors are tuned to the movements of swimming prey by chemoreceptors." *Science,* 243, 1585-1591.
19. Watson, G. M., and Hessinger, D. A. (1992). "Receptors for N-acetylated sugars may stimulate adenylate cyclase to sensitize and tune mechanoreceptors involved in triggering nematocyst discharge." *Exp Cell Res,* 198(1), 8-16.
20. Weber, J. (1989). "Nematocysts (stinging capsules of Cnidaria) as Donnan-potential-dominated osmotic systems." *Eur J Biochem,* 184(2), 465-76.
21. Westfall, J. A., Bradbury, P. C., and Townsend, J. W. (1983). "Ultrastructure of the dinoflagellate Polykrikos. I. Development of the nematocyst-taeniocyst complex and morphology of the site for extrusion." *J Cell Sci,* 63, 245-61.

What is claimed is:

1. A composition-of-matter comprising a therapeutic or a cosmetic agent and a tentacle, an organ or a part thereof, wherein said tentacle, organ or part thereof contains stinging cells comprising stinging capsules.
2. The composition-of-matter of claim 1, wherein said therapeutic or cosmetic agent is disposed in a liquid surrounding, or stored within, said stinging capsules.
3. The composition-of-matter of claim 1, wherein said therapeutic agent is a prodrug activatable prior to, during or following discharge of said stinging capsules.
4. The composition-of-matter of claim 1, wherein said tentacle, organ or part thereof is derived from an organism of a class selected from the group consisting of Anthozoa, Hydrozoa and Scyphozoa.
5. The composition-of-matter of claim 1, wherein said tentacle, organ or part thereof is derived from an organism of a phylum selected from the group consisting of Cnidaria, Dinoflagellata and Myxozoa.
6. The composition of claim 1, wherein said therapeutic agent is selected from the group consisting of an antibiotic, an anti fungal agent, an anti-viral agent, a scabicide agent.
7. The composition of claim 1, wherein said cosmetic agent is selected from the group consisting of an anti-wrinkling agent, an anti-acne agent, a skin peel agent, a hair follicle stimulating agent and a hair follicle suppressing agent.
8. A pharmaceutical composition comprising the composition-of-matter of claim 1.
9. The pharmaceutical composition of claim 8, further comprising a pharmaceutically acceptable carrier selected from the group consisting of an aqueous solution, a gel, an oil and semi solid formulation.
10. The composition of matter of claim 1, wherein said therapeutic agent comprises a retinoid agent.
11. The composition of matter of claim 6, wherein said antiviral agent is a non-nucleoside reverse transcriptase inhibitor.
12. The composition of matter of claim 1, wherein said therapeutic agent is a nucleic acid construct.
13. The composition of matter of claim 12, wherein said nucleic acid construct comprises a polynucleotide selected from the group consisting of an antisense polynucleotide and a ribozyme.
14. The composition of matter of claim 1, wherein said therapeutic agent is selected from the group consisting of a non-steroidal anti inflammatory drug, an immunosuppressant, an anti-histamine agent, an anti-puritic agent and a psoralen.
15. The composition of matter of claim 1, wherein said therapeutic agent is a vaccine.
16. The composition of matter of claim 1, wherein said therapeutic agent is an enzyme.
17. The composition of matter of claim 1, wherein said therapeutic agent is a hormone.
18. The composition of matter of claim 1, wherein said therapeutic agent is an antibody.
19. The composition of matter of claim 1, wherein said therapeutic agent is a growth factor.

* * * * *